US008362899B2

(12) United States Patent
Hutzler et al.

(10) Patent No.: US 8,362,899 B2
(45) Date of Patent: Jan. 29, 2013

(54) INITIATING EMERGENCY COMMUNICATION IN RESPONSE TO DETECTING BIO-FEEDBACK SATISFYING AN ALERT CONDITION (75) Inventors: Richard Hutzler, Ocean Shores, WA (US); Mary E. Montano, Tucson, AZ (US); William King Morse, Tucson, AZ (US); Steve Ngoe Nguyen, Pflugerville, TX (US); Nelson Jay Smith, IV, Tucson, AZ (US); Gregory Carson Windsor, Portland, OR (US)

(73) Assignee: International Business Machines Corporation, Armonk, NY (US)

( * ) Notice: Subject to any disclaimer, the term of this patent is extended or adjusted under 35 U.S.C. 154(b) by 272 days.

(21) Appl. No.: 12/402,474

(22) Filed: Mar. 11, 2009

(65) Prior Publication Data
US 2010/0231379 A1    Sep. 16, 2010

(51) Int. Cl.
*H04Q 1/30* (2006.01)
(52) U.S. Cl. ............ 340/539.12; 455/404.1; 455/404.2; 600/301; 600/532
(58) Field of Classification Search .......... 340/539.12; 455/404.1–404.2; 60/301, 532
See application file for complete search history.

(56) References Cited

U.S. PATENT DOCUMENTS

| 5,726,636 | A | 3/1998 | Hayes, Jr. |
| 5,742,666 | A | 4/1998 | Alpert |
| 6,532,366 | B1 | 3/2003 | Chung et al. |
| 7,092,695 | B1 | 8/2006 | Boling et al. |
| 7,181,229 | B2 | 2/2007 | Singh et al. |
| 7,274,924 | B2 | 9/2007 | Yoshioka |
| 2004/0239524 | A1* | 12/2004 | Kobayashi ............... 340/870.07 |
| 2005/0208925 | A1* | 9/2005 | Panasik et al. ............ 455/404.1 |
| 2006/0040639 | A1 | 2/2006 | Karl et al. |
| 2006/0058697 | A1* | 3/2006 | Mochizuki et al. .......... 600/532 |
| 2007/0099559 | A1 | 5/2007 | Huang et al. |
| 2009/0054937 | A1* | 2/2009 | Severin et al. .................... 607/5 |
| 2009/0171170 | A1* | 7/2009 | Li et al. ......................... 600/301 |
| 2010/0253505 | A1* | 10/2010 | Chou ....................... 340/539.12 |

OTHER PUBLICATIONS

Health and Well Being, "Smart Clothing that Takes Biochemical Medical Observations Through the Day", May 28, 2007, [retrieved online Jan. 23, 2009] http:www.gizmag.com/go/7333/.
BBC News, "Smart Clothes to Monitor Health", Jun. 11, 2007, [retrieved online Jan. 23, 2009], http://newsvote.bbc.co.uk/mpapps/pagetools/print/news.bbc.co.uk/2/hi/he . . . .

* cited by examiner

*Primary Examiner* — George Bugg
*Assistant Examiner* — Ojiako Nwugo
(74) *Attorney, Agent, or Firm* — David W. Victor; Konrad Raynes Davda & Victor LLP (57) ABSTRACT Provided are a method, system, and program for initiating emergency communication in response to detecting bio-feedback satisfying an alert condition. A portable electronic device is coupled to a body of a user to monitor biofeedback from the body of the user through a monitoring device disposed within the portable electronic device. Detection is made that that the monitored biofeedback satisfies an alert condition. An operation is initiated to cause a wireless transmission of an emergency communication to an emergency station in response to detecting that the monitored biofeedback satisfies the alert condition.

21 Claims, 6 Drawing Sheets

INITIATING EMERGENCY COMMUNICATION IN RESPONSE TO DETECTING BIO-FEEDBACK SATISFYING AN ALERT CONDITION

BACKGROUND OF THE INVENTION

1. Field of the Invention

The present invention relates to a method, system, and article of manufacture for initiating emergency communication in response to detecting bio-feedback satisfying an alert condition.

2. Description of the Related Art

People living with chronic illnesses may need to suddenly contact emergency services for medical assistance. "Home based" systems provide the user a medallion style of emergency call device, which may be worn around the neck, that the user must manually activate to send a signal to a base station that generates a call for emergency services and response. Some of these "home based" systems are tied into the use of smoke detectors and home security systems, and will make an emergency call even if the user cannot. The user medallion may signal a base station in the user home that makes an emergency call through the user's phone line.

These "home based" emergency call systems typically use a land line and require the user and their call device or medallion to remain within a close distance to a base station. For instance, the emergency medallion may not be able to make an emergency call when the user is away from home or outside the reception range of the base station.

There is a need in the art for improved systems that initiate an emergency call or communication for users experiencing a medical emergency.

SUMMARY

Provided are a method, system, and program for initiating emergency communication in response to detecting bio-feedback satisfying an alert condition. A portable electronic device is coupled to a body of a user to monitor biofeedback from the body of the user through a monitoring device disposed within the portable electronic device. Detection is made that that the monitored biofeedback satisfies an alert condition. An operation is initiated to cause a wireless transmission of an emergency communication to an emergency station in response to detecting that the monitored biofeedback satisfies the alert condition.

DETAILED DESCRIPTION

Figure 1:
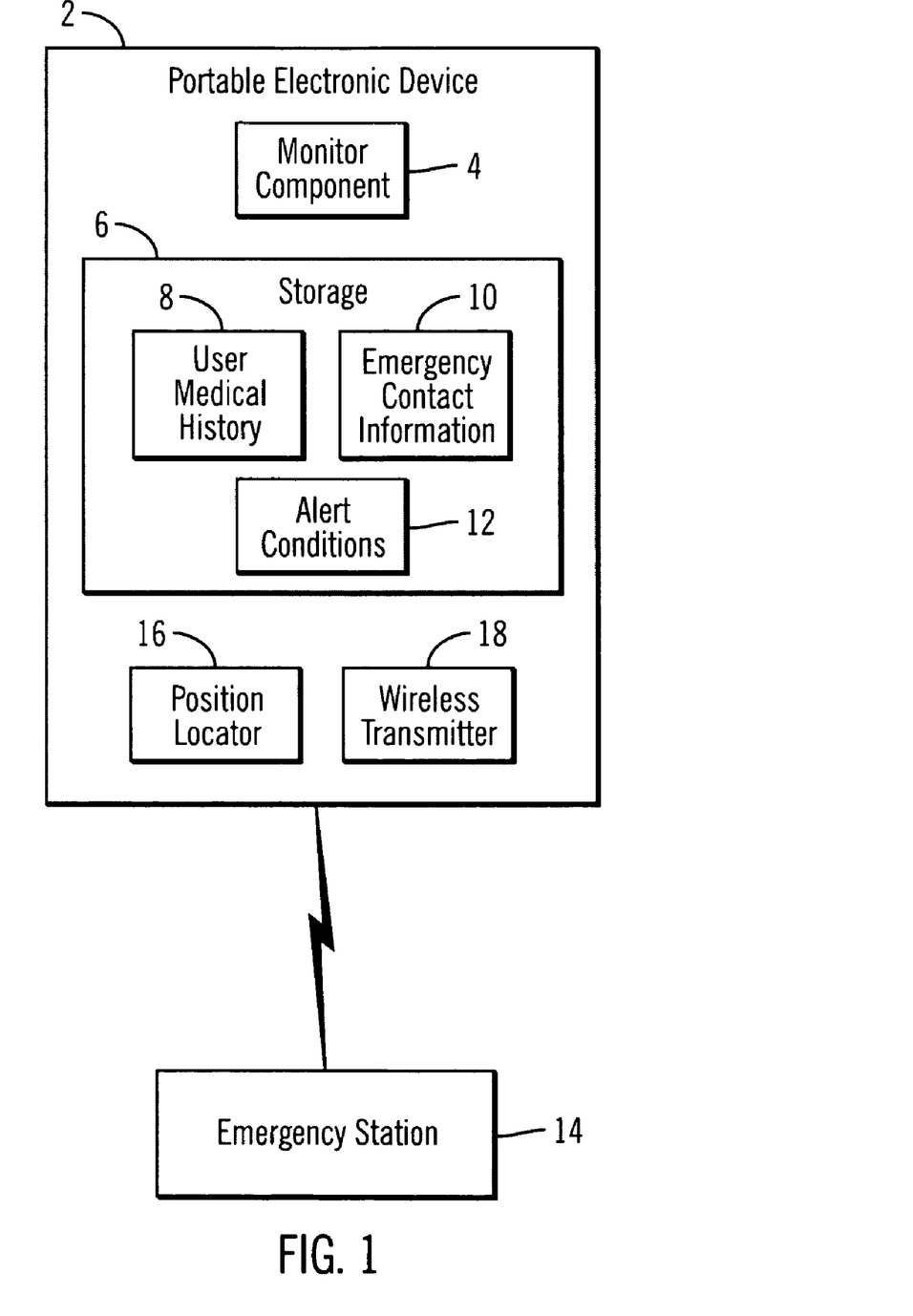
FIG. 1 illustrates an embodiment of a portable electronic device communication with an emergency station.

FIG. 1 illustrates an embodiment of a computing environment. A portable electronic device 2 includes a monitor component 4 to monitor biofeedback from a body of a person to which the portable electronic device 2 is coupled. The monitor component 4 may include a sensor (not shown) to measure bio-feedback from the person wearing the portable electronic device 2. For instance, the monitor component 4 may include a sensor for monitoring biofeedback, such as detecting a pulse or analyze a biochemical measurement, such as monitoring sweat including the pH, salinity and perspiration rate of the user to which the portable electronic device 2 is coupled. Other examples of monitored biofeedback include, but are not limited to, a cardio-rhythm, insulin level, heart rate, electrolytes, keytones, and blood level with respect to a monitored chemical. For instance, the monitor component 4 may determine whether the user has a certain chemical or chemical level for law enforcement purposes, such as blood-alcohol level, an illegal substance, etc.

The sensor may comprise a subdermal sensor (completely buried in the skin), transdermal sensor (placed under the skin but also protrude out) and/or dermal sensor (in contact with the outer layer of the skin, but not under the skin). The portable electronic device 2 further includes a storage 6 having a user medical history 8, emergency contact information 10 for the user, and alert conditions 12. The user medical history 8 may include important medical information for the user of the device 2, such as allergies, medications, doctor names, next of kin contact, etc. The emergency contact information 10 for a remote emergency station 14, such as a emergency medical service provider, an ambulance service, 911, etc, may comprise a phone number, network address, instant message address, radio frequency, etc. Alert conditions 12 may comprise parameters that indicate when measured bio-feedback from the monitor component 4 reaches a level at which the emergency station 14 should be alerted. For instance, the alert condition 12 may specify a parameter for a measured pulse rate to determine when the heart rate becomes too high or low indicating a problem with the heart rate or for measured biochemical feedback indicates another alarming health situation. For instance, the blood sugar level may be measured to determine whether the user is experiencing a serious health situation.

The portable electronic device 2 may further include a position locator 16, such as a Global Positioning System (GPS) locator, to determine a geographical position of the portable electronic device 2, and a wireless transmitter 18 to engage in wireless communication with a remote location or device, such as with a receiver at an emergency station 14. The wireless transmitter 18 may comprise a transceiver for employing wireless communication technology, such as cellular phone communication, wireless local area network (e.g., WLAN), Bluetooth, two-way radio, cordless telephone communication, satellite, etc.

Figure 2:
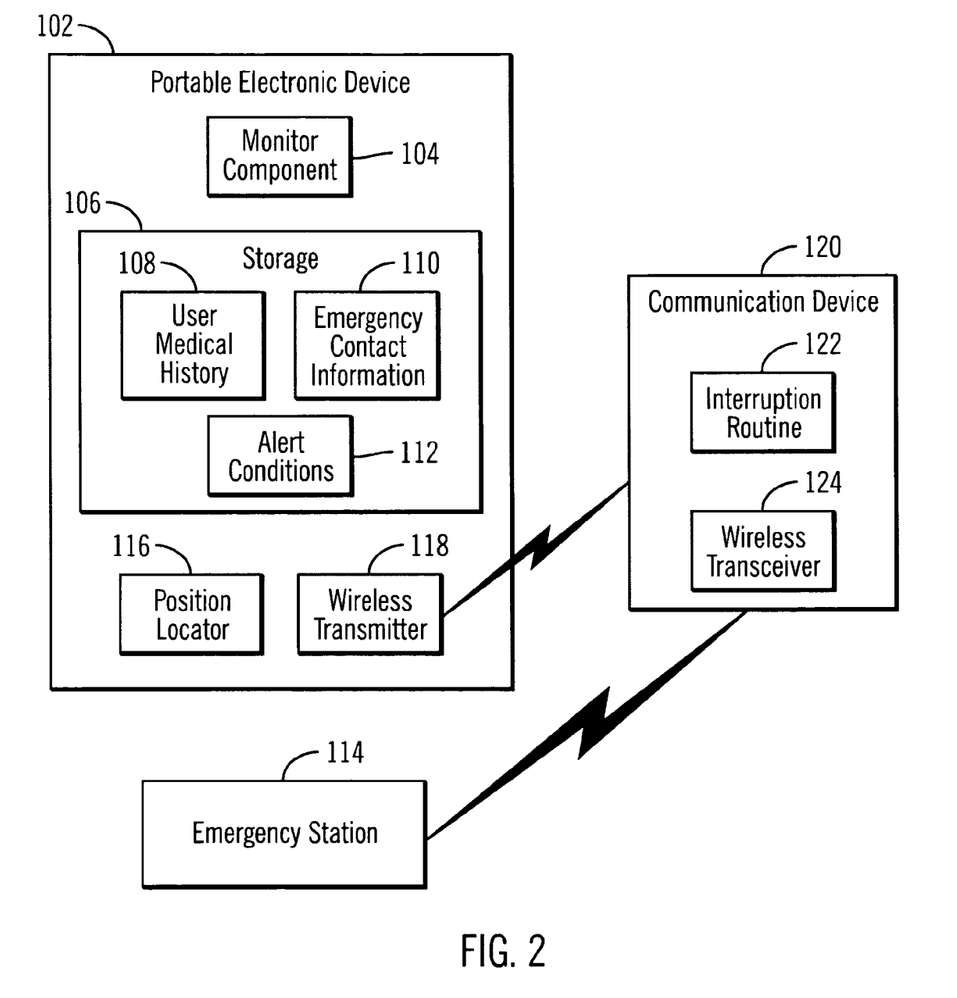
FIG. 2 illustrates an embodiment of a portable electronic device communication with an emergency station via a communication device.

FIG. 2 illustrates an additional embodiment of a portable electronic device 102 including components 104, 106, 108, 110, 112, 116, and 118 which are described with respect to components 4, 6, 8, 10, 12, 16, and 18, respectively, in FIG. 1. In the embodiment of FIG. 2, upon detecting that biofeedback monitored by the monitor component 104 satisfies a parameter of an alert condition 112, the wireless transmitter 118 generates an emergency communication and communicates a command with the emergency communication, such as information on the satisfied alert condition, geographical position as determined by position locator 116, user medical history 108, and/or emergency contact information 110 to an external communication device 120 to cause the communication device 120 to communicate the emergency communication to an emergency station 114, which may comprise the emergency station 14 described with respect to FIG. 1.

The communication device 120 may comprise a cellular phone, pager, telephony device or other type of device capable of communicating with the emergency station 114. The communication device includes an interruption routine 122 and a wireless transceiver 124. The interruption routine 122 executes code to interrupt communication device 120 operations so that the communication device 120 may send the emergency communication on the alert condition for the user of the portable electronic device 102 to the emergency station 114. For instance, if the communication device 120 comprises a telephone (cellular or otherwise), then the interruption routine 122 may interrupt a current communication between the communication device 120 and a remote communication device, such as another telephone, web site, etc., to allow the communication device 120 to send the emergency communication to the emergency station 114. The wireless transceiver 124 includes the capability to transmit and receive communications in one or more wireless communication protocols. Alternatively, the transceiver 124 may comprise an adaptor for wired connections as well as wireless communications.

In the embodiment of FIG. 2, the user medical history 108, emergency contact information 110, and position locator 116 are included in the portable electronic device 102. In an alternative embodiment, the information 108, 110 and/or position locator 116 may be maintained in the communication device 120. In such case, the emergency communication may be generated partially in the portable electronic device 102 and the communication device 120, depending on whether the information 108, 110 and position locator 116 are maintained at the communication device 120.

In certain embodiments, the wireless transmitter 118 may use a communication interface having a limited distance, such as Bluetooth, radio frequency, etc., to communicate with the communication device 120, and the communication device 120 may utilize a more long distance communication interface to communicate with the emergency station 114, such as cellular phone, local area network (LAN), WLAN, the public switched telephone network (PSTN), etc. In certain embodiments, the communication device 120 may comprise a portable device, such as the cellular phone of the user, or comprise a stationary device, such as a module located in a building or the home of the user of the portable electronic device 2 to receive emergency communications from the portable electronic device 2.

Figure 4:
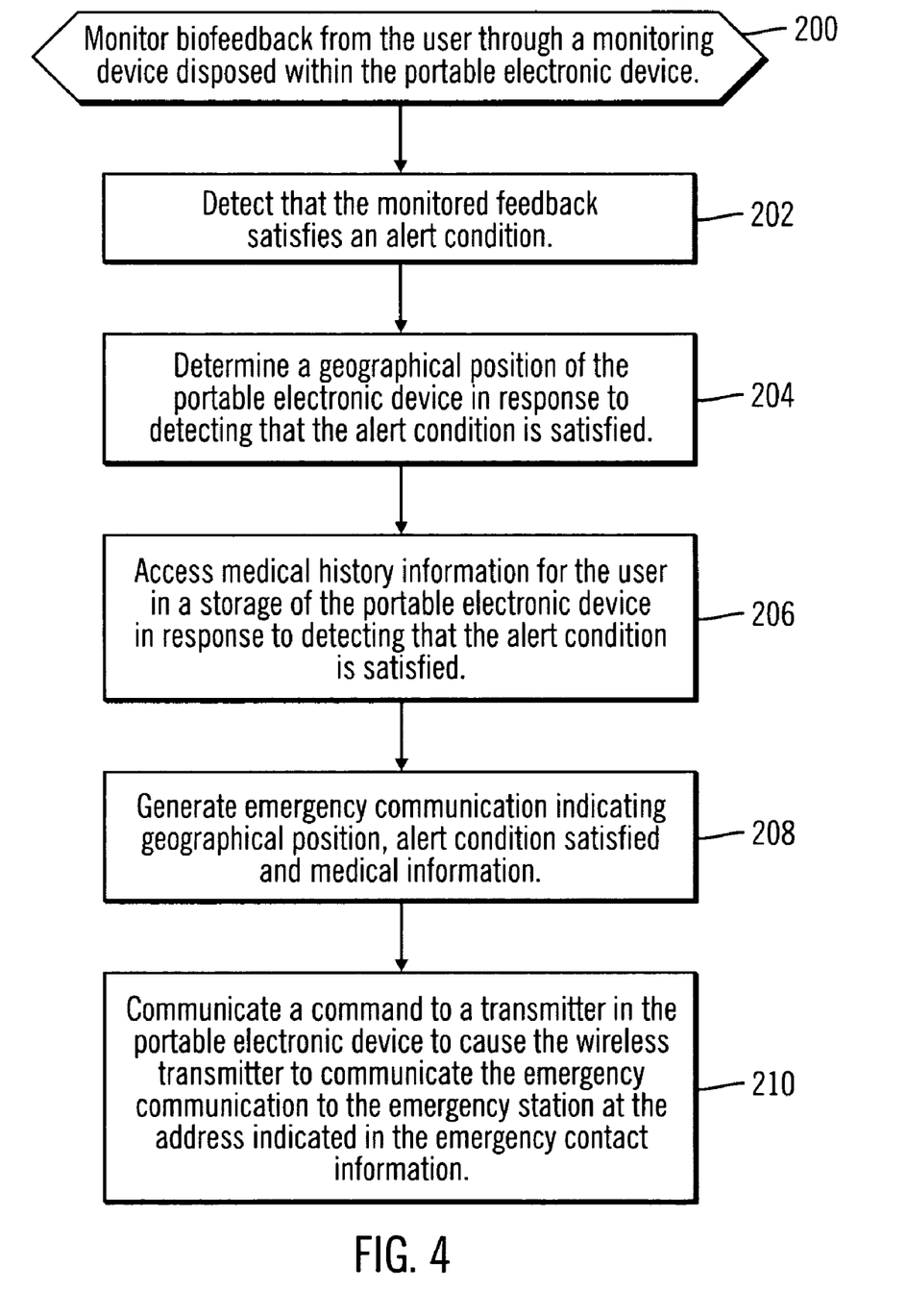
FIGS. 4 and 5 illustrate embodiments of operations performed by a portable electronic device in response to detecting that an alert condition is satisfied.
Figure 5:
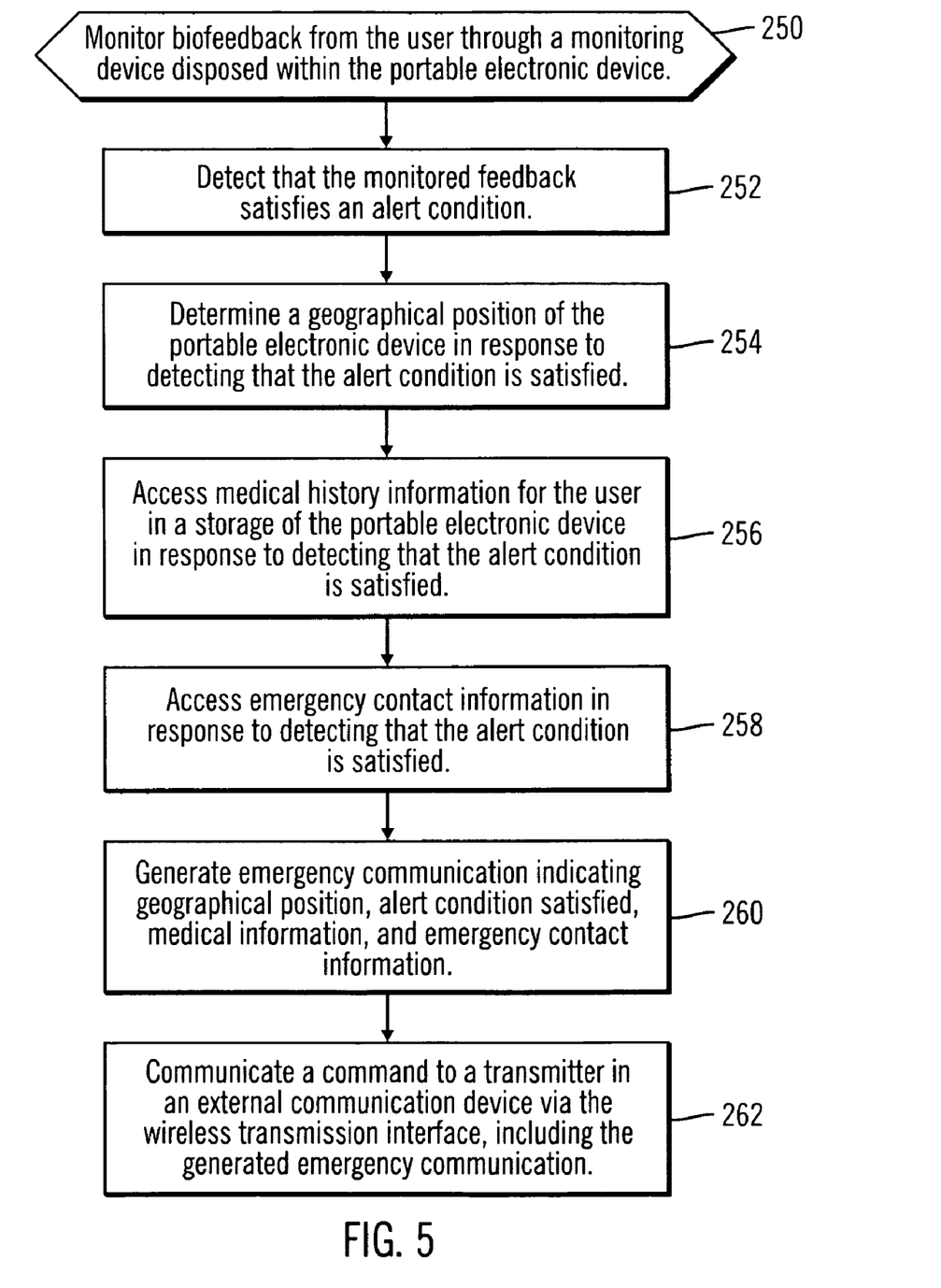
Figure 6:
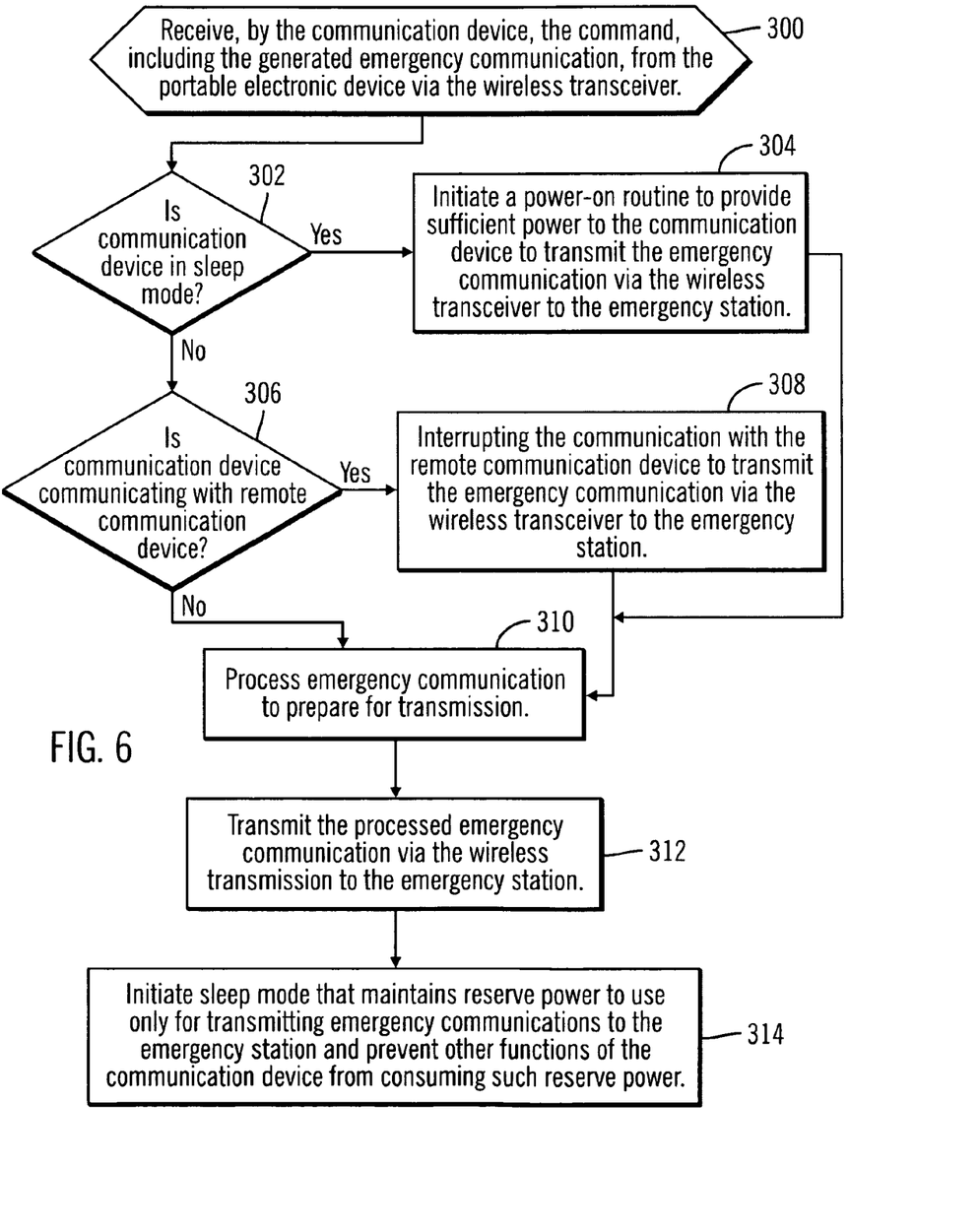
FIG. 6 illustrates an embodiment of operations performed by a communication device to forward an emergency communication from a portable electronic device to an emergency station.

The devices 2, 102, and 120 may include a processor that executes programs loaded into a memory to perform operations, such as those described with respect to FIGS. 4, 5, and 6, respectively. Alternatively, the devices 2, 102, and 120 may include hardware components, such as an Application Specific Integrated Circuit (ASIC), to perform the operations described with respect to FIGS. 4, 5, and 6 or include a combination of a processor executing code and hardware components to perform the described operations.

Figure 3:
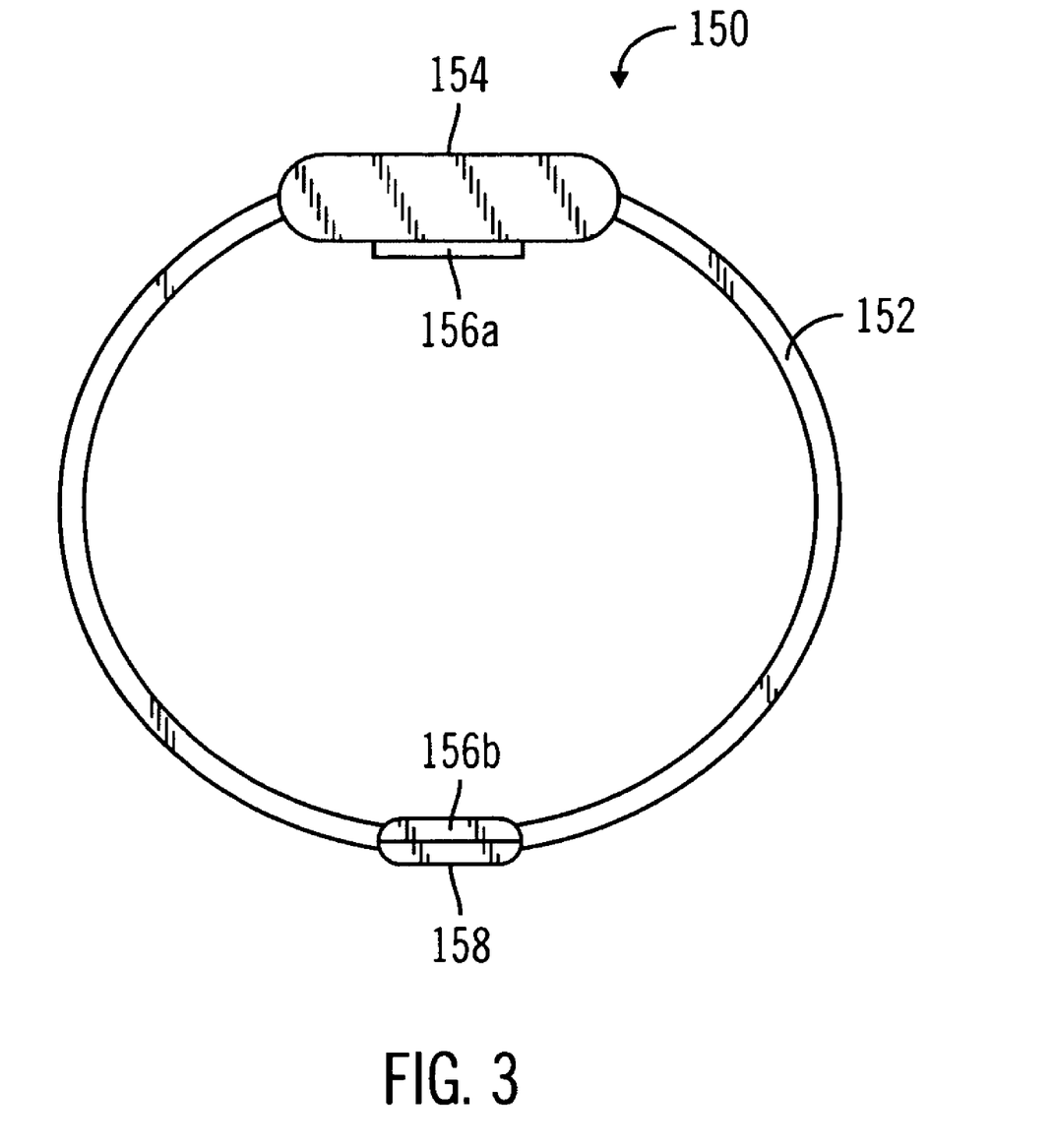
FIG. 3 illustrates an embodiment of a portable electronic device for monitoring bio-feedback in a wrist band.

FIG. 3 illustrates an embodiment where the portable electronic device 2, 102 may be implemented in a wristwatch 150. The wristband 152 may include an antenna to enable communication with the emergency station 14 or a communication device 102 (FIG. 2). The watch portion 154 may include the electronic components of the portable electronic device 2, 102, such as components 4, 6, 8, 10, 12, 16, 18 (FIG. 1) or 104, 106, 108, 110, 112, 118 (FIG. 2), and may optionally include other functions, such as a watch, stopwatch, sports heart rate monitor, etc. Biofeedback sensors 156a, 156b may be coupled to the watch portion 154, such as sensor 156a, and a buckle 158, such as sensor 156b. The sensors 156a, 156b may be dermal, subdermal and/or transdermal and may communicate biofeedback information to a monitor component 4, 104 in the watch portion 124.

FIG. 4 illustrates an embodiment of operations performed by the electronic portable device 2 (FIG. 1). Biofeedback is monitored (at block 200) from the user by the monitor component 4 disposed within the portable electronic device 2. The electronic portable device 2 detects (at block 200) that the monitored feedback satisfies an alert condition 12. An alert condition may be satisfied if a measured biofeedback value, e.g., a heart rate, is determined to be above or below or equal to a certain value. The alert condition 12 may comprise a biofeedback parameter and a comparison operator, e.g., greater than, less than, equal, etc., such that if the measured biofeedback parameter satisfies the alert condition 12, emergency communication is initiated.

If the alert condition is satisfied, then the electronic portable device 2, through the position locator 16, determines (at block 204) a geographical position of the portable electronic device 2 and accesses (at block 206) the user medical history information 8 for the user in the storage 6. The portable electronic device 2 generates (at block 208) an emergency communication indicating the determined geographical position, information on the alert condition that was satisfied, and the accessed medical information. The portable electronic device 2 communicates (at bock 210) a command to the wireless transmitter 18 to cause the wireless transmitter 18 to communicate the generated emergency communication to the emergency station 14 at the address indicated in the emergency contact information 10, which may comprise a telephone number, network address, radio frequency, etc.

FIG. 5 illustrates an embodiment of operations performed by the electronic portable device 102 (FIG. 2). Biofeedback is monitored (at block 250) from the user by the monitor component 104 disposed within the portable electronic device 102. The electronic portable device 102 detects (at block 252) that the monitored feedback satisfies an alert condition. An alert condition 112 may be satisfied if a measured biofeedback value, e.g., a heart rate, is determined to be above or below or equal to a certain value. The alert condition 112 may comprise a biofeedback parameter and a comparison operator, e.g., greater than, less than, equal, etc., such that if the measured biofeedback parameter satisfies the alert condition 112, emergency communication is initiated.

If (at block 252) the alert condition 112 is satisfied, then the electronic portable device 102, through the position locator 116, determines (at block 254) a geographical position of the portable electronic device 102 and accesses (at block 256) the user medical history information 208 and emergency contact information 110 (at block 258) for the user in the storage 206. The portable electronic device 102 generates (at block 260) an emergency communication indicating geographical position, alert condition satisfied, user medical history 108, and emergency contact information 110 and communicates (at bock 208) a command and the generated emergency communication to the wireless transmitter 118 to cause the wireless transmitter 118 to communicate the emergency communication to the communication device 120 to forward to the emergency station 114 about the detected alert condition, including the determined geographical position and the accessed medical history information.

In certain embodiments, part of the emergency communication, such as the geographical position, alert condition satisfied, medical information, and/or emergency contact information may be generated by the communication device 120 if the communication device includes the user medical history 108, emergency contact information 110 and/or the position locator 116.

FIG. 6 illustrates an embodiment of operations performed by the communication device 120 to forward the emergency communication concerning the satisfied alert condition detected by the portable electronic device 102 with respect to biofeedback from a user of the device 102 to the emergency station 114. Upon the communication device 120 receiving (at block 300) the command, including the generated emergency communication, from the portable electronic device 102b via the wireless transceiver 124, the interruption routine 122 determines (at block 302) whether the communication device is in a sleep mode. A sleep mode comprises a power management mode where the system cuts power to all unneeded parts of the device. Those components that need to retain power to restore to a fully operational state, such as the memory, continue to receive power in the sleep mode. If so, the interruption routine 122 initiates (at block 304) a power-on routine to provide sufficient power to the communication device 120 to transmit the emergency communication via the wireless transmission to the emergency station. If (at block 302) the device 120 is not in sleep mode, then the interruption routine 122 determines (at block 306) whether the communication device 120 is in communication with a remote communication device. If so, then the interruption routine 122 interrupts (at block 308) the communication with the remote communication device to transmit the emergency communication via the wireless transceiver 124 to the emergency station 114.

From blocks 304 or 308 or if the communication device 120 is ready to communicate (from the no branch of block 306), control proceeds to block 310 where the communication device 120 processes (at block 310) the emergency communication from the portable electronic device 102 to prepare for transmission via the wireless transceiver 124 to the emergency station 114. The communication device 120 may process the emergency communication by modifying or adding headers to transmit to the emergency station 114 using a transmission protocol used by the emergency station 114, or add information such as user medical history 108, position information of the user or communication device 120, etc. The wireless transceiver 124 transmits (at block 312) the processed emergency communication to the emergency station 114. In certain embodiments, the communication device 120 may initiate (at block 314) a sleep mode that maintains reserve power to use only for transmitting emergency communications to the emergency station 114. In this reserve power mode, the communication device 120 would prevent other functions of the communication device 120 from consuming such reserve power.

With described embodiments, a device coupled to the body of a user or patient monitors the user biofeedback information and if an alert condition or situation is detected, transmits an emergency communication to the emergency station 14 directly or to a communication device 120 used by the user or available to receive emergency communications, such that the communication device 120 forwards the emergency communication to an emergency station 114 to handle and provide emergency services to the user if necessary.

Additional Embodiment Details

The described operations may be implemented as a method, apparatus or article of manufacture using standard programming and/or engineering techniques to produce software, firmware, hardware, or any combination thereof. The described operations may be implemented as code maintained in a "computer readable medium", where a processor may read and execute the code from the computer readable medium. A computer readable medium may comprise media such as magnetic storage medium (e.g., hard disk drives, floppy disks, tape, etc.), optical storage (CD-ROMs, DVDs, optical disks, etc.), volatile and non-volatile memory devices (e.g., EEPROMs, ROMs, PROMs, RAMs, DRAMs, SRAMs, Flash Memory, firmware, programmable logic, etc.), etc. The code implementing the described operations may further be implemented in hardware logic (e.g., an integrated circuit chip, Programmable Gate Array (PGA), Application Specific Integrated Circuit (ASIC), etc.). Still further, the code implementing the described operations may be implemented in "transmission signals", where transmission signals may propagate through space or through a transmission media, such as an optical fiber, copper wire, etc. The transmission signals in which the code or logic is encoded may further comprise a wireless signal, satellite transmission, radio waves, infrared signals, Bluetooth, etc. The transmission signals in which the code or logic is encoded is capable of being transmitted by a transmitting station and received by a receiving station, where the code or logic encoded in the transmission signal may be decoded and stored in hardware or a computer readable medium at the receiving and transmitting stations or devices. An "article of manufacture" comprises computer readable medium, hardware logic, and/or transmission signals in which code may be implemented. A device in which the code implementing the described embodiments of operations is encoded may comprise a computer readable medium or hardware logic. Of course, those skilled in the art will recognize that many modifications may be made to this configuration without departing from the scope of the present invention, and that the article of manufacture may comprise suitable information bearing medium known in the art.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the present invention need not include the device itself.

The illustrated operations of FIGS. 4, 5, and 6 show certain events occurring in a certain order. In alternative embodiments, certain operations may be performed in a different order, modified or removed. Moreover, steps may be added to the above described logic and still conform to the described embodiments. Further, operations described herein may occur sequentially or certain operations may be processed in parallel. Yet further, operations may be performed by a single processing unit or by distributed processing units.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. The above specification, examples and data provide a complete description of the manufacture and use of the composition of the invention. Since many embodiments of the invention can be made without departing from the spirit and scope of the invention, the invention resides in the claims hereinafter appended.

What is claimed is:

1. A method implemented in a portable electronic device coupled to a body of a user and a communication device, comprising:
   monitoring biofeedback from the body of the user through a monitoring device disposed within the portable electronic device;
   detecting that the monitored biofeedback satisfies an alert condition; and
   initiating an operation to have a wireless transmission interface in the portable electronic device communicate a command to a transmitter located in the communication device external to the portable electronic device to cause the transmitter to communicate a wireless transmission of an emergency communication to an emergency station in response to detecting that the monitored biofeedback satisfies the alert condition, wherein the wireless transmission interface in the portable electronic device has a limited transmission distance as compared to the transmitter in the communication device which transmits over longer distances than the wireless transmission interface.

2. The method of claim 1, wherein the communication to the emergency station is about the detected alert condition.

3. The method of claim 1, further comprising:
   receiving, by the communication device, the command from the portable electronic device via the wireless transmission interface while the communication device is in a sleep mode; and
   initiating, by the communication device, a power-on routine to provide sufficient power to transmit the emergency communication via the wireless transmission to the emergency station.

4. The method of claim 3, further comprising:
   maintaining, by the communication device, reserve power to use for only emergency communications to the emergency station.

5. The method of claim 1, further comprising:
   receiving, by the communication device, the command from the portable electronic device via the wireless transmission interface while the communication device is communicating with a remote communication device; and
   interrupting, by the communication device, the communication with the remote communication device to transmit the emergency communication via the wireless transmission to the emergency station.

6. The method of claim 1, wherein the monitored biofeedback comprises at least one of a cardio-rhythm, insulin level, heart rate, electrolytes, keytones, and blood level with respect to a monitored chemical.

7. The method of claim 1, wherein the communication device comprises a cellular telephone and wherein the wireless transmission interface in the portable electronic device uses radio frequency transmissions.

8. A method implemented in a portable electronic device coupled to a body of a user and a communication device, comprising:
   monitoring biofeedback from the body of the user through a monitoring device disposed within the portable electronic device;
   detecting that the monitored biofeedback satisfies an alert condition;
   determining, at the portable electronic device, a geographical position of the portable electronic device in response to detecting that the alert condition is satisfied;
   initiating an operation to have a wireless transmission interface in the portable electronic device communicate a command to a transmitter located in the communication device external to the portable electronic device to cause the transmitter to communicate a wireless transmission of an emergency communication including the determined geographical position to an emergency station in response to detecting that the monitored biofeedback satisfies the alert condition, wherein the wireless transmission interface in the portable electronic device has a limited transmission distance as compared to the transmitter in the communication device which transmits over longer distances than the wireless transmission interface.

9. A method implemented in a portable electronic device coupled to a body of a user and a communication device, comprising:
   monitoring biofeedback from the body of the user through a monitoring device disposed within the portable electronic device;
   detecting that the monitored biofeedback satisfies an alert condition;
   accessing medical history information for the user in a storage of the portable electronic device in response to detecting that the alert condition is satisfied, wherein the medical history information includes personal medical history information separate from the monitored biofeedback; and initiating an operation to have a wireless transmission interface in the portable electronic device communicate a command to a transmitter located in the communication device external to the portable electronic device to cause the transmitter to communicate a wireless transmission of an emergency communication to an emergency station including the accessed medical history information in response to detecting that the monitored biofeedback satisfies the alert condition, wherein the wireless transmission interface in the portable electronic device has a limited transmission distance as compared to the transmitter in the communication device which transmits over longer distances than the wireless transmission interface.

10. A system for monitoring a body of a user in communication with an emergency station, comprising:

a communication device having a transmitter; and a portable electronic device, external to the communication device, coupled to the body of a user, comprising:
  a monitoring device monitoring biofeedback from the body of the user;
  a wireless transmission interface;
  a monitor component coupled to the monitoring device and including code executed to perform operations, the operations comprising:
    detecting that the monitored biofeedback satisfies an alert condition; and
    initiating an operation to have the wireless transmission interface communicate a command to the transmitter to cause the transmitter to communicate a wireless transmission of an emergency communication to the emergency station in response to detecting that the monitored biofeedback satisfies the alert condition, wherein the wireless transmission interface in the portable electronic device has a limited transmission distance as compared to the transmitter in the communication device which transmits over longer distances than the wireless transmission interface.

11. The system of claim 10, wherein the communication with the emergency station is about the detected alert condition.

12. The system of claim 10, wherein the communication device receives the command from the portable electronic device via the wireless transmission interface while the communication device is in a sleep mode, and wherein the command causes the communication device to initiate a power-on routine to provide sufficient power to transmit the emergency communication via the wireless transmission to the emergency station.

13. The system of claim 10, further comprising:
a position locator for determining a geographical position of the portable electronic device in response to detecting that the alert condition is satisfied, wherein initiating the operation to cause the wireless transmission further comprises including the determined geographical position in the emergency communication.

14. The system of claim 10, further comprising:
a storage having medical history information for the user, wherein the monitor component further performs accessing the medical history information for the user in response to detecting that the alert condition is satisfied, wherein the medical history information includes personal medical history information separate from the monitored biofeedback, wherein initiating the operation to cause the wireless transmission further comprises including the accessed medical history information in the emergency communication.

15. The system of claim 10, wherein the communication device comprises a cellular telephone and wherein the wireless transmission interface in the portable electronic device uses radio frequency transmissions.

16. An article of manufacture comprising at least one of a magnetic storage, optical storage, memory device, flash memory and hardware logic having code executed by a portable electronic device coupled to a body of a user and a communication device to perform operations, the operations comprising:
monitoring biofeedback from the body of the user through a monitoring device disposed within the portable electronic device;
detecting that the monitored biofeedback satisfies an alert condition; and
initiating an operation to have a wireless transmission interface in the portable electronic device communicate a command to a transmitter located in the communication device external to the portable electronic device to cause the transmitter to communicate a wireless transmission of an emergency communication to an emergency station in response to detecting that the monitored biofeedback satisfies the alert condition, wherein the wireless transmission interface in the portable electronic device has a limited transmission distance as compared to the transmitter in the communication device which transmits over longer distances than the wireless transmission interface.

17. The article of manufacture of claim 16, wherein the communication to the emergency station is about the detected alert condition.

18. The article of manufacture of claim 16, wherein the communication device receives the command from the portable electronic device via the wireless transmission interface while the communication device is in a sleep mode, and wherein the command causes the communication device to initiate a power-on routine to provide sufficient power to transmit the emergency communication via the wireless transmission to the emergency station.

19. The article of manufacture of claim 16, wherein the operations further comprise:
determining a geographical position of the portable electronic device in response to detecting that the alert condition is satisfied, wherein initiating the operation to cause the wireless transmission further comprises including the determined geographical position in the emergency communication.

20. The article of manufacture of claim 16, wherein the operations comprise:
accessing medical history information for the user in a storage of the portable electronic device in response to detecting that the alert condition is satisfied, wherein the medical history information includes personal medical history information separate from the monitored biofeedback, wherein initiating the operation to cause the wireless transmission further comprises including the accessed medical history information in the emergency communication.

21. The article of manufacture of claim 16, wherein the communication device comprises a cellular telephone and wherein the wireless transmission interface in the portable electronic device uses radio frequency transmissions.

* * * * *